United States Patent
Larsen et al.

(10) Patent No.: US 9,321,793 B2
(45) Date of Patent: Apr. 26, 2016

(54) PURIFICATION OF CHLOROSILANES USING CHROMATOGRAPHY

(71) Applicant: Dow Corning Corporation, Midland, MI (US)

(72) Inventors: Robert Thomas Larsen, Midland, MI (US); Michael W. Toepke, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/400,575

(22) PCT Filed: May 1, 2013

(86) PCT No.: PCT/US2013/039048
§ 371 (c)(1),
(2) Date: Nov. 12, 2014

(87) PCT Pub. No.: WO2013/169537
PCT Pub. Date: Nov. 14, 2013

(65) Prior Publication Data
US 2015/0141688 A1    May 21, 2015

Related U.S. Application Data

(60) Provisional application No. 61/643,991, filed on May 8, 2012.

(51) Int. Cl.
*C07F 7/12* (2006.01)
*C07F 7/20* (2006.01)
*B01D 15/18* (2006.01)
*B01D 15/32* (2006.01)

(52) U.S. Cl.
CPC ............... *C07F 7/20* (2013.01); *B01D 15/185* (2013.01); *B01D 15/322* (2013.01); *B01D 15/325* (2013.01)

(58) Field of Classification Search
USPC .................................. 556/451, 452, 465, 466
See application file for complete search history.

(56) References Cited

U.S. PATENT DOCUMENTS 5,567,836 A * 10/1996 Diaz et al. ...................... 556/466
5,569,775 A * 10/1996 Diaz et al. ...................... 556/466

FOREIGN PATENT DOCUMENTS

| JP | 53-065828 | | 6/1978 | |
| JP | 53065828 | * | 6/1978 | ............... C07F 7/20 |
| JP | 53-111015 | | 9/1978 | |
| JP | 53111015 | * | 9/1978 | ............... C07F 7/20 |

* cited by examiner

*Primary Examiner* — Sudhakar Katakam
*Assistant Examiner* — Pancham Bakshi
(74) *Attorney, Agent, or Firm* — Matthew Fewkes

(57) ABSTRACT

The present invention relates to a method for separating organohalosilanes. The method includes introducing a mixture including at least a first organohalosilane and a second organohalosilane onto a chromatographic bed including a stationary phase. The method also includes passing a liquid mobile phase through the chromatographic bed to produce an eluate including at least one fraction enriched in the first organohalosilane and at least one fraction enriched in the second organohalosilane.

13 Claims, 3 Drawing Sheets

PURIFICATION OF CHLOROSILANES USING CHROMATOGRAPHY

CROSS REFERENCE TO RELATED APPLICATIONS

This application is a U.S. national stage filing under 35 U.S.C. §371 of PCT Application No. PCT/US13/39048 filed on 1 May 2013, which claims the benefit of U.S. Provisional Patent Application No. 61/643,991 filed 8 May 2012 under 35 U.S.C. §119 (e). PCT Application No. PCT/US13/39048 and U.S. Provisional Patent Application No. 61/643,991 are hereby incorporated by reference.

Organohalosilanes are generally produced as a mixture of compounds which then can be separated into the individual organohalosilanes. The Direct Process (also called the Direct Synthesis, the Rochow Process, or the Müller-Rochow Process) is the most common method of producing organohalosilanes on an industrial scale. This process produces a stream containing a mixture including methylchlorosilanes. Although the major products are typically dimethyldichlorosilane and methyltrichlorosilane, other products include trimethylchlorosilane, methyldichlorosilane, and dimethylchlorosilane. Separation of the organohalosilanes is a vital step in the process. Typically, fractional distillation is used to separate organohalosilanes. Due to the problematic close boiling points of several of the products (e.g. dimethyldichlorosilane b.p. 70.1° C., methyltrichlorosilane b.p. 66.1° C.), a large number of separation stages and high reflux ratios are required. Once separated, the individual silanes are useful for the preparation of siloxane polymers as well as certain specialized applications.

SUMMARY OF THE INVENTION

Distillation methods of separating methylchlorosilanes based on small differences in boiling points are both difficult to accomplish and expensive. Employing distillation columns having high separating capacities, using a large number of distillation separation stages, and using high reflux ratios requires a large amount of expensive equipment that can take up a great deal of space and also can consume a large amount of energy to operate. Prior work in the field has focused on the optimization of the distillation process. For instance, distillation aids have been used to change the relative volatility of species within the crude silane product to enhance separation. The present invention provides an advantageous alternative to distillation methods of separating organohalosilanes.

The present invention provides for the separation of organohalosilanes by the use of liquid chromatography. Various embodiments of the present invention have surprising advantages over other methods of separating organohalosilanes, such as traditional distillation. Generally, it is assumed that as compared to a distillation method, chromatography is a low-throughput procedure. However, surprisingly, embodiments of the present method can provide high-throughput separation of organohalosilanes. Generally, it is assumed that organohalosilanes are reactive with chromatography stationary media. Organohalosilanes can be extremely reactive materials that usually must be handled in an anhydrous environment if undesired chemical reactions are to be avoided. However, surprisingly, some embodiments of the present method can be used to separate organohalosilanes with limited or no undesired chemical reactions between the organohalosilanes and the stationary media. Generally, when faced with the industrial separation of volatile molecules and small molecules those of ordinary skill in the art of separation look immediately to common industrial separation options, namely distillation and liquid-liquid extraction rather than chromatography. However, surprisingly, some embodiments can be used to separate volatile organohalosilanes. Some embodiments of the present invention, as compared to a distillation process that provides a similar degree of separation, can surprisingly provide separation of organohalosilanes with at least one of: greater energy efficiency, higher yield, higher purity, uses equipment that takes up less space, and uses equipment that is less expensive to provide, operate, or maintain.

Distillation generally uses elevated temperature conditions, in order to boil components to be separated. Elevated temperatures can cause reactive compounds such as organohalosilanes to participate in undesired chemical reactions, leading to decreases in yield. However, some embodiments of the present invention can separate organohalosilanes at about room temperature, avoiding undesired chemical reactions caused by elevated temperature, such as decomposition, chemical rearrangement, or other reactions. The elevated temperatures used in some distillation procedures can cause increased corrosive effects of certain materials, such as for example, organohalosilanes. Corrosion of equipment can cause decreased yield, increase the cost and complexity of equipment design, and increase the frequency with which equipment needs to be replaced. However, some embodiments of the present invention can separate organohalosilanes at about room temperature, decreasing negative effects associated with corrosion. It can be difficult using distillation procedures to separate organohalosilanes having close boiling points. However, some embodiments of the present invention can be used to effectively separate organohalosilanes having close boiling points. Some toxic or strictly regulated materials produced during certain organohalosilane synthetic procedures can be difficult to remove. However, some embodiments of the present invention can be used to more easily or effectively separate some byproducts of certain organohalosilane synthetic procedures, allowing, for example, greater freedom to utilize a synthetic method of choice without the need to use expensive or tedious separation procedures. Various embodiments of the present invention can separate chiral organohalosilanes from one another, such separations are not possible using liquid-liquid extraction. In some embodiments, the liquid chromatographic method can be used to achieve purities not otherwise achievable by distillation, absorption, or other separation methods.

In an absorption technique, an absorptive material (e.g. silica gel or other materials sometimes used in chromatography as the stationary phase) is contacted uniformly with a solution containing a mixture including components desired to be separated and having evenly distributed concentrations of the components throughout the absorptive material. Subsequently, the solution is removed from the absorptive material, giving a solution that has a lower concentration of any component that is absorbed to the absorptive material more than other components. However, embodiments of the present invention have certain differences and advantages over an absorption technique. Absorptive techniques are generally only useful for generating two fractions, one fraction containing compounds not as attracted to the absorptive material, and another fraction containing compounds more attracted to the absorptive material. In contrast, a chromatographic technique can produce an essentially infinite number of fractions, allowing for separation of any suitable number of materials to any suitable level of precision. A non-continuous absorptive method only allows the system of the absorptive material and the mixture to come to a single equilibrium state, such that if the stationary phase used in the absorptive method has a maximum capacity for retaining a particular component (e.g. can become saturated), or can experience a decreased capacity for the particular component upon exposure to one or more components, the stationary phase is evenly affected with this deficiency and the particular component is not effectively separated from the rest of the mixture. Due to saturation or decreased capacity, absorptive techniques have a limited ability to remove greater than minimal amounts of particular components that are attracted to the absorptive material. In contrast, liquid chromatography allows the stationary phase, the components to be separated, and the mobile phase to reach an infinite number of equilibriums. Liquid chromatography contacts different portions of the stationary phase with different concentrations of the components to be separated, caused by the uneven attraction of different components to the stationary phase as the mobile phase flows by, allowing for separation of materials that have more similar polarities than can be effectively separated using an absorptive technique. In liquid chromatography, as the components are moved along the stationary phase a component that is attracted to the stationary phase can be repeatedly confronted with fresh stationary phase that has maximum ability to retain the component, allowing for, for example, separation of larger quantities of one material from another (e.g. wherein the component that is more attracted to the stationary phase is present in more than a minor amount), or more complete separation of one material from another, as compared to an absorptive technique.

In some embodiments, the method can be used as the primary purification method, bringing crude organohalosilanes forward all the way to a required range of purity. In some embodiments, the present method can be used to bring organohalosilanes to an intermediate range of purity, with the final purification steps performed by a different process, such as a distillation process. In other embodiments, the present method can be used to bring organohalosilanes to a final or near-final required range of purity from an intermediate state of purity, such as an intermediate state of purity that may follow a distillation process or other separation process.

Various embodiments provide a liquid chromatography method for separating organohalosilanes. The method includes introducing a mixture onto a chromatographic bed. The mixture includes at least a first organohalosilane and a second organohalosilane. The chromatographic bed includes a stationary phase. The method also includes passing a liquid mobile phase through the chromatographic bed. Passing the liquid through the chromatographic bed produces an eluate. The eluate includes at least one fraction enriched in the first organohalosilane. The eluate also includes at least one fraction enriched in the second organohalosilane.

Various embodiments provide a liquid chromatography method for separating organohalosilanes. The method includes introducing a mixture onto a chromatographic bed. The mixture includes at least dimethyldichlorosilane and methyltrichlorosilane. The chromatographic bed includes a stationary phase. The mixture includes dimethyldichlorosilane and methyltrichlorosilane in a mole ratio of from about $10^6:1$ to about $10^{-6}:1$. The method also includes passing a liquid mobile phase through the chromatographic bed to produce an eluate. The eluate includes at least one fraction enriched in dimethydichlorosilane. The eluate also includes at least one fraction enriched in methyltrichlorosilane. The method also includes recovering the at least one fraction enriched in dimethydichlorosilane and the at least one fraction enriched in methyltrichlorosilane.

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

Figure 1:
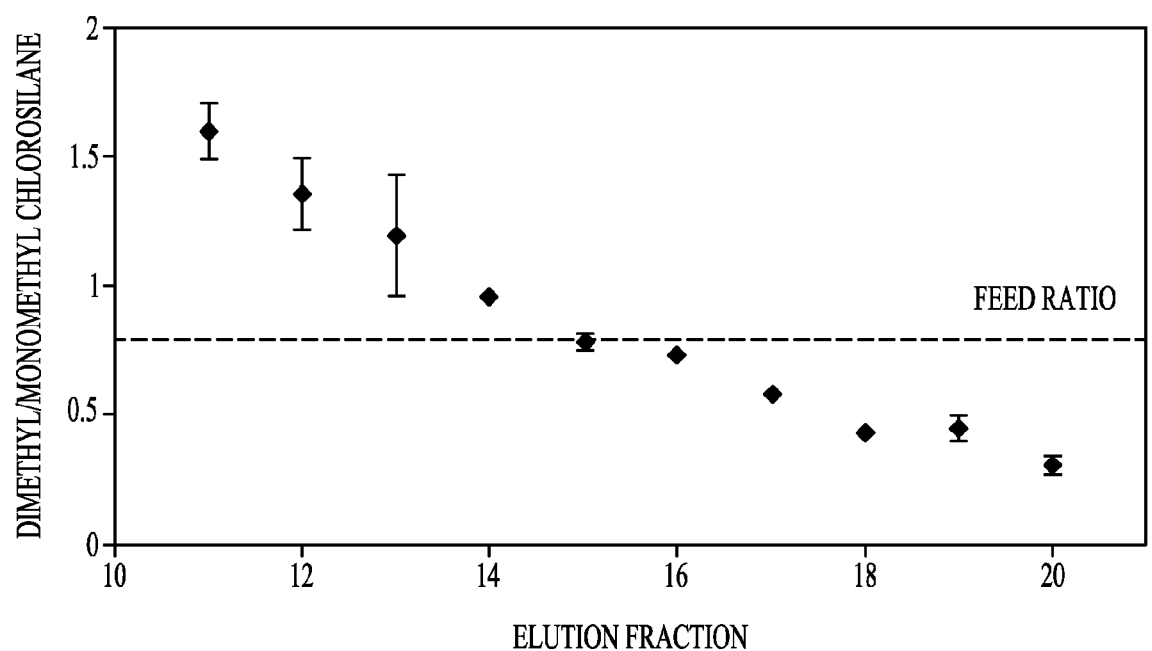
FIG. 1 illustrates the ratio of dimethyldichlorosilane to methyltrichlorosilane in the eluate to the fraction eluted from a column, in accordance with various embodiments.
Figure 2A:
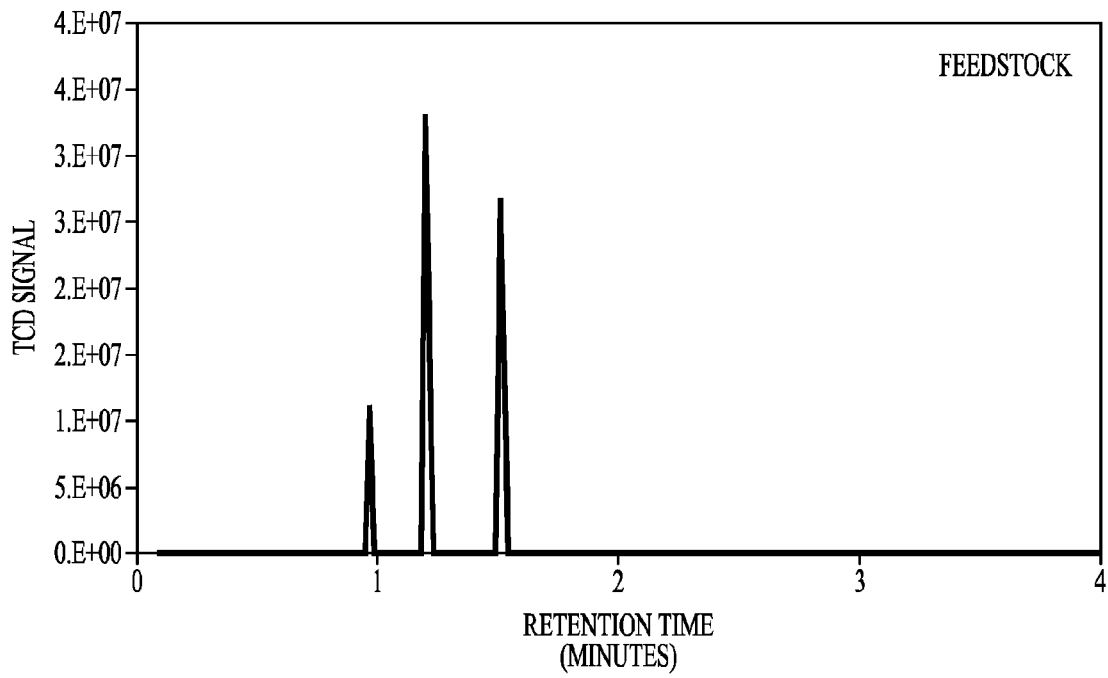
FIG. 2A illustrates GC peaks for a feedstock, in accordance with various embodiments.
Figure 2B:
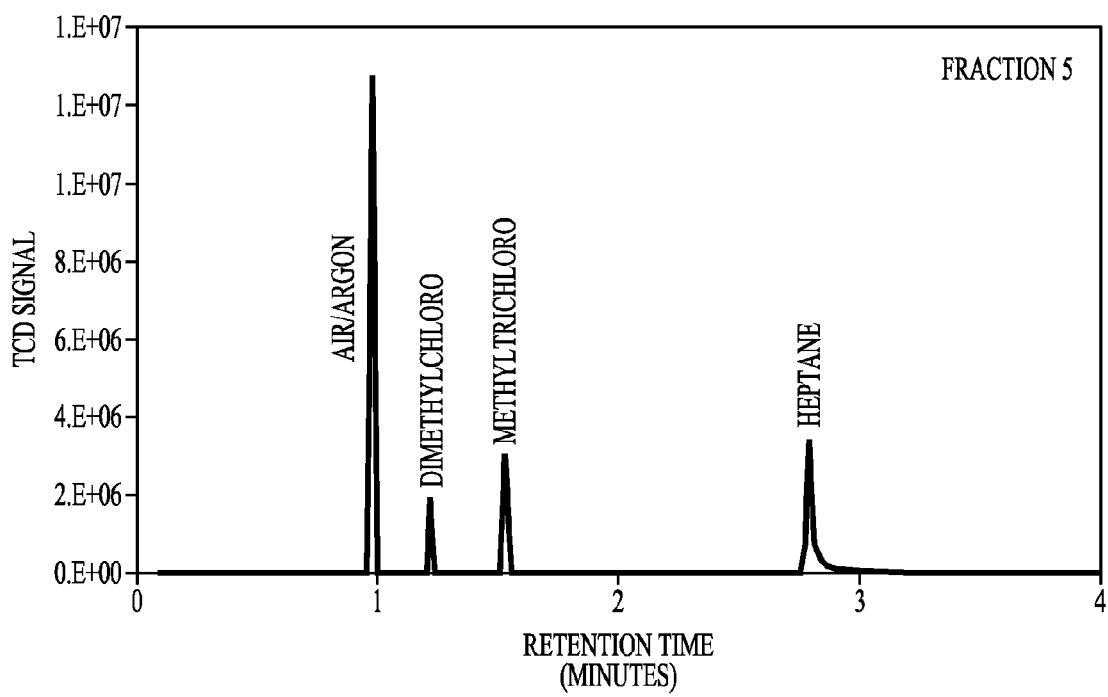
FIG. 2B illustrates GC peaks for fraction 5 eluted from a column, in accordance with various embodiments.
Figure 2C:
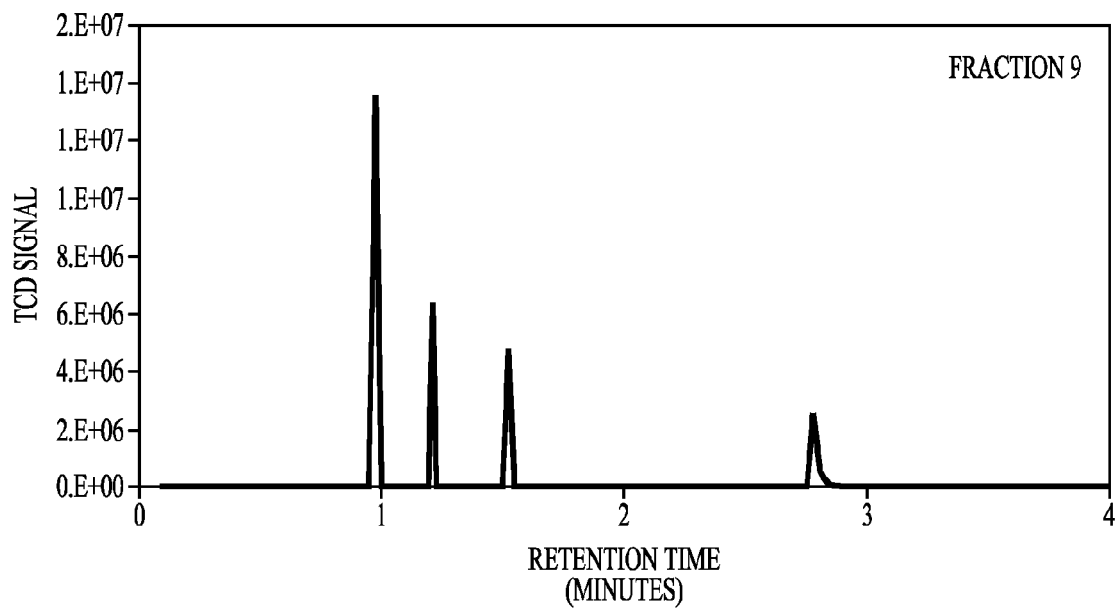
FIG. 2C illustrates GC peaks for fraction 9 eluted from a column, in accordance with various embodiments.
Figure 2D:
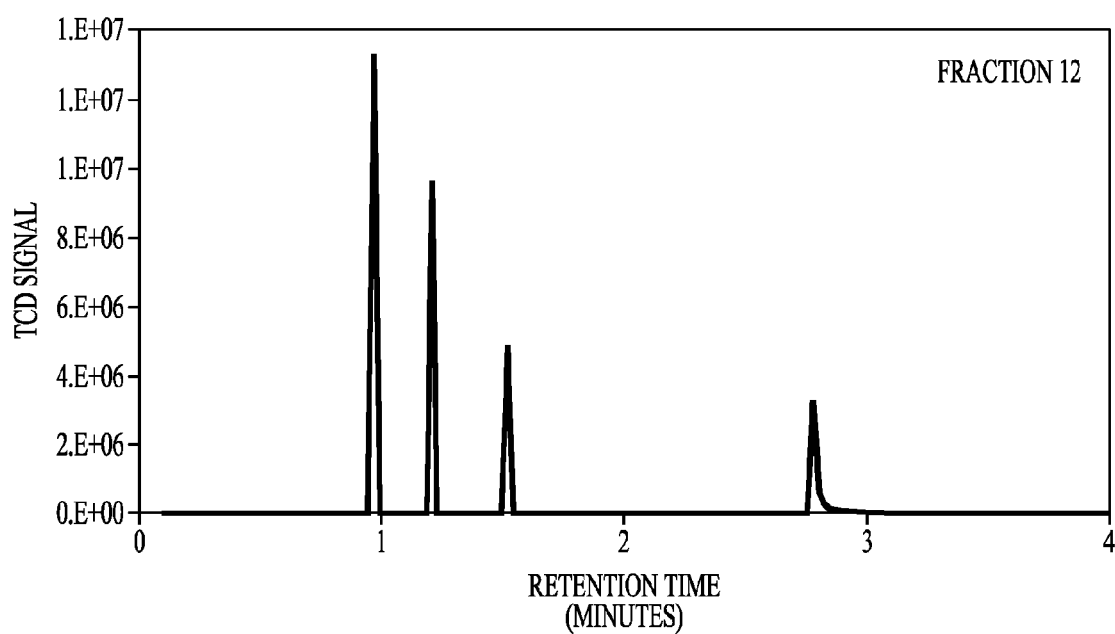
FIG. 2D illustrates GC peaks for fraction 12 eluted from a column, in accordance with various embodiments.

Reference will now be made in detail to certain claims of the disclosed subject matter, examples of which are illustrated in the accompanying drawings. While the disclosed subject matter will be described in conjunction with the enumerated claims, it will be understood that they are not intended to limit the disclosed subject matter to those claims. On the contrary, the disclosed subject matter is intended to cover all alternatives, modifications, and equivalents, which can be included within the scope of the presently disclosed subject matter as defined by the claims.

References in the specification to "one embodiment," "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one of ordinary skill in the art to effect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.1% to 0.5%, 1.1% to 2.2%, 3.3% to 4.4%) within the indicated range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The term "organic group" as used herein refers to but is not limited to any carbon-containing functional group.

As used herein, "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

As used herein, "chromatographic bed" refers to the stationary phase in an encasement, such as to form a packed column or a packed bed. The chromatographic bed can include mobile phase, the mixture to be separated, other packing materials such as a frit, cotton, or sand, a combination thereof, or can include only stationary phase.

As used herein, "stationary phase" refers to the chromatography media in a liquid chromatographic method that does not move during elution of the chromatographic bed.

As used herein, "mobile phase" refers to the solvent phase in a liquid chromatographic method that moves during elution of the chromatographic bed.

As used herein, "eluate" refers to the mobile phase leaving or that has left the chromatographic bed. As the mobile phase leaves the chromatographic bed, it can include various proportions of the materials being separated.

As used herein, "elute," "elution," or "eluting" refers to the passing of a mobile phase through the stationary phase of a chromatographic bed. As the mobile phase passes through the chromatographic bed, it can include various proportions of the materials being separated.

As used herein, "silica gel" refers to silica dioxide ($SiO_2$) and polysiloxane networks having any suitable degree of branching. Branched polysiloxane networks in silica gel can terminate in —OH groups. In bonded silica gels, one or more of the —OH groups can be functionalized. In some embodiments, substantially all —OH groups can be functionalized. In other embodiments, substantially none or only some of the —OH groups can be functionalized.

Method for Separation of Organohalosilanes

Various embodiments of the present invention include a liquid chromatography method for separating a mixture including at least a first organohalosilane and a second organohalosilane. Various embodiments of the present invention provide an organohalosilane separated using an embodiment of the present method. Herein, "separation" as provided by embodiments of the present invention can be any degree of partial separation, or a complete separation. The liquid chromatography method includes a mobile phase, which can be any suitable solvent or combination of solvents. The liquid chromatography method includes a chromatographic bed that includes a solid stationary phase, which can be any suitable stationary phase. In some examples, the stationary phase can be dried or anhydrous, to help avoid undesired chemical reactions with the organohalosilanes. The stationary phase can be in any suitable encasement, such as a column or a packed bed. The method includes introducing the mixture including at least a first organohalosilane and a second organohalosilane onto the chromatographic bed. The method includes passing (e.g. eluting) the mobile phase through the stationary phase. The method can take advantage of different relative amounts of attraction of one organohalosilane versus another organohalosilane for the stationary phase versus the mobile phase. The composition of the mobile phase can be altered during the liquid chromatography process to achieve a desired separation. In other embodiments, the composition of the mobile phase can remain constant during the method, to achieve a desired separation.

In one embodiment, the mixture including at least a first organohalosilane and a second organohalosilane is introduced onto a packed bed and eluted using a mobile phase. The first organohalosilane and second organohalosilane exit the packed bed at different speeds based on their relative affinities for the packing material versus the mobile phase. In another example, dimethyldichlorosilane can be separated from methyltrichlorosilane by passing a mixture including the two organohalosilanes through a chromatographic bed including a stationary phase such as magnesium silicate (normal-phase) or alkyl-bonded silica (reversed-phase) and eluting the organohalosilanes with an appropriate mobile phase.

The mixture to be separated can be any suitable mixture including at least a first organohalosilane and a second organohalosilane. As used herein, an organohalosilane refers to any compound including a silicon atom bound to at least one halogen and also bound to at least one monovalent hydrocarbon group. Examples of organohalosilanes include compounds described by the formula $R_aH_bSiX_{4-a-b}$, where a=0 to 3, b=0 to 3, a+b=0 to 3, X is a halogen and R is a monovalent hydrocarbon group including one to 12 carbon atoms. In some examples, X is a chloride. The monovalent hydrocarbon groups represented by R typically have from 1 to 10 carbon atoms, alternatively from 1 to 6 carbon atoms, alternatively from 1 to 4 carbon atoms. Examples of hydrocarbyl groups represented by R include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl; cycloalkyl, such as cyclopentyl, cyclohexyl, and methylcyclohexyl; aryl, such as phenyl and naphthyl; alkaryl, such as tolyl and xylyl; aralkyl, such as benzyl and phenethyl; alkenyl, such as vinyl, allyl, and propenyl, butenyl, hexenyl, and octenyl; arylalkenyl, such as styryl and cinnamyl; and alkynyl, such as ethynyl and propynyl. In some examples, the organohalosilane is trimethylchlorosilane, dimethyldichlorosilane, methyltrichlorosilane, dimethylchlorosilane, phenylmethyldichlorosilane, phenyltrichlorosilane, trichlorosilane, tetrachlorosilane, methylvinyldichlorosilane or dimethyldivinylchlorosilane.

Various embodiments encompass any suitable scale. In some examples, the method can separate a mixture including at least a first organohalosilane and a second organohalosilane wherein the mixture has a mass that is less than or equal to about 0.000,001 g, or 0.000,01 g, 0.000,1 g, 0.001 g, 0.01 g, 0.1 g, 1 g, 2 g, 3 g, 4 g, 5 g, 10 g, 25 g, 100 g, 200 g, 300 g, 400 g, 500 g, 1000 g, 1500 g, 5000 g, 10 kg, 20 kg, 30 kg, 40 kg, 50 kg, 100 kg 500 kg, 1000 kg, 2000 kg, 3000 kg, 4000 kg, 5000 kg, 10,000 kg, 50,000 kg, 100,000 kg, 500,000 kg, or less than or equal to about 1,000,000 kg or more.

In addition to the at least a first organohalosilane and a second organohalosilane, the mixture can contain any other compound or combination of compounds, such as one or more additional different organohalosilanes, other byproducts of organohalosilane synthesis, an organic compound, or combination of organic compounds. The first organohalosilane can be any suitable organohalosilane. The second organohalosilane can be any suitable organohalsilane. In some examples, the first organohalosilane is dimethyldichlorosilane, and the second organohalosilane is methyltrichlorosilane. In some embodiments, the mixture to be separated into enriched fractions can include methytrichlorosilane and dimethyldichlorosilane in a mole ratio of about $10^{12}:1$ to about $10^{-12}:1$, or about $10^6:1$ to about $10^{-6}:1$. In some examples, the first organohalosilane is methyltrichlorosilane, and the second organohalosilane is dimethylchlorosilane. In some embodiments, the mixture to be separated into enriched fractions can include methyltrichlorosilane and dimethylchlorosilane in a mole ratio of from $10^{12}:1$ to about $10^{-12}:1$, or about $10^6:1$ to about $10^{-6}:1$.

The stationary phase can be any suitable stationary phase used for liquid chromatography, such as is familiar to one of ordinary skill in the art. For example, the stationary phase can be a stationary phase for normal-phase liquid chromatography, or for reverse-phase liquid chromatography, further examples for which are given herein. The stationary phase can be any material that allows the elution of the mobile phase and to which each of the first organohalosilane and the second organohalosilane in the mixture have a different attraction as compared to the mobile phase. Suitable stationary phases can include silica gel, bonded silica gel, or alumina. Further examples of suitable stationary phases are given herein. The stationary phase can have any suitable particle size. For example, the average particle size of the stationary phase can equal to or less than about 1 µm, 5 µm, 10 µm, 50 µm, 100 µm, 150 µm, 200 µm, 250 µm, 300 µm, 350 µm, 400 µm, 450 µm, 500 µm, 600 µm, 700 µm, 800 µm, 900 µm, 1 mm, 2 mm, 3 mm, 4 mm, 5 mm, 10 mm, about 50 mm, or more. The stationary phase can have any suitable surface area. For example, the average surface area of the stationary phase can be equal to or less than about 1 m$^2$/g, 10 m$^2$/g, 20 m$^2$/g, 50 m$^2$/g, 100 m$^2$/g, 150 m$^2$/g, 200 m$^2$/g, 250 m$^2$/g, 300 m$^2$/g, 350 m$^2$/g, 400 m$^2$/g, 450 m$^2$/g, 500 m$^2$/g, 550 m$^2$/g, 600 m$^2$/g, 700 m$^2$/g, 800 m$^2$/g, 900 m$^2$/g, 1000 m$^2$/g, or more. The stationary phase can have any suitable average pore size, and any suitable range of pore sizes. For example, the stationary phase can have a pore size of equal to or less than about 1 Å, 2 Å, 5 Å, 10 Å, 20 Å, 30 Å, 40 Å, 50 Å, 60 Å, 70 Å, 80 Å, 90 Å, 100 Å, 150 Å, 200 Å, 250 Å, 300 Å, 500 Å, 750 Å, 1000 Å, 1 µm, 10 µm, 25 µm, 50 µm, 75 µm, or about 100 µm or more, or any combination thereof. The stationary phase can have any suitable range of pore volume, and any suitable range of pore volumes. For example, the stationary phase can have a pore volume equal to or less than about 0.01 cm$^3$/g, 0.1 cm$^3$/g, 0.2 cm$^3$/g, 0.3 cm$^3$/g, 0.4 cm$^3$/g, 0.5 cm$^3$/g, 0.6 cm$^3$/g, 0.7 cm$^3$/g, 0.8 cm$^3$/g, 0.9 cm$^3$/g, 1.0 cm$^3$/g, 1.5 cm$^3$/g, 2.0 cm$^3$/g, 5.0 cm$^3$/g, 10.0 cm$^3$/g.

The chromatographic bed can form a column. As one of ordinary skill in the art will readily recognize, liquid chromatography is generally performed in a cylindrical encasement having the shape of a column. The encasement can be any suitable material, such as, for example, glass, metal, plastic, and the like. Any suitable column shape can be used. A taller column can be used, for example, to increase the residence time of the mixture in the stationary phase as the mobile phase is eluted at a given rate. A wider column can be used, for example, to allow for the use of a greater quantity of stationary phase for a given column height. In some examples, increasing the quantity of stationary phase for a given column height or increasing the residence time at a given elution rate can allow for the separation of a larger amount of the mixture to be separated or it can allow for the desired degree of separation of a first and second organohalosilane that have smaller differences in relative attraction to the mobile phase versus the stationary phase. The height of the column can be any suitable height, such as less than or equal to 100 mm, 250 mm, 500 mm, 750 mm, 1 m, 2 m, 3 m, 4 m, 5 m, 6 m, 7 m, 8 m, 9 m, 10 m, 11 m, 12 m, 13 m, 14 m, or about 15 m, or more. In some embodiments, a column can have any suitable height, including by using several discrete columns linked together that function as a single column in effect. The diameter of the column can be any suitable diameter, such as less than or equal to 1 mm, 5 mm, 10 mm, 20 mm, 30 mm, 40 mm, 50 mm, 60 mm, 70 mm, 80 mm, 90 mm, 100 mm, 120 mm, 140 mm, 160 mm, 180 mm, 200 mm, 250 mm, 500 mm, 750 mm, 1 m, 2 m, 3 m, 4 m, 5 m, 6 m, 7 m, 8 m, 9 m, or about 10 m, or more.

In some embodiments, prior to introduction of the mixture including at least a first organohalosilane and a second organohalosilane onto the chromatographic bed, the chromatographic bed can be prepared. Preparing the chromatographic bed can include adding the stationary phase to the encasement, e.g. to a column or bed. In some embodiments, a material or medium can be added to the encasement prior to addition of the stationary phase that can help to prevent elution of the stationary phase with the mobile phase, such as for example cotton, sand, a glass frit, retaining plate, mesh, or other suitable materials. In some embodiments, flow distributors can be used to prevent flow channeling. Preparing the chromatographic bed can include adding a mobile phase to the chromatographic bed. In some embodiments, the mobile phase can be added at the same time as the stationary phase, for example as a slurry. In some embodiments, the mobile phase can be added before or after the stationary phase is added. In some examples, pressure can be used to cause the mobile phase to flow through the stationary phase at a suitable rate during column preparation; in other examples, gravity alone can be used with no pressure during column preparation. In some embodiments, a material or medium can be added to the top of the stationary phase prior to introduction of the mixture to be separated that can help prevent the top of the stationary phase from being disturbed during introduction of the mixture. Suitable materials or medium can include, for example, cotton, sand, a glass frit, retaining plate, mesh, or other suitable materials. In some embodiments, prior to introduction of the mixture onto the stationary bed, the level of the top of the mobile phase in the encasement can be adjusted to be about the same level as the top of the stationary phase; in other embodiments, the level of the mobile phase in the encasement can be any suitable level with respect to the top of the stationary phase. The mobile phase used during preparation of the chromatographic bed can include the same solvent or ratio of solvents used during initial elution of the chromatographic bed, or a different solvent or ratio of solvents than used during initial elution of the chromatographic bed.

The mixture including at least a first organohalosilane and a second organohalosilane can be introduced onto the chromatographic bed in any suitable fashion. In some examples, the mixture can be introduced neat onto the chromatographic bed. In some examples, the mixture can be diluted with a suitable solvent prior to introduction onto the bed. Suitable solvents for dilution can include, for example, methylene chloride. In some embodiments, the mixture can be introduced onto the chromatographic bed in a slurry of stationary phase added directly on top of the prepared chromatographic bed.

After introduction of the mixture onto the chromatographic bed, the passing (e.g. elution) of the mobile phase through the stationary phase can begin. During the elution process, mobile phase is added to the top of the chromatographic bed and allowed to flow through the stationary phase, after which the mobile phase can exit the column. As the mobile phase is passed through the column, the first and second organohalosilanes in the mixture pass through the column at different rates depending on their relative attractions to the stationary phase versus the mobile phase. An organohalosilane that is more attracted to the mobile phase versus the stationary phase will pass through the column faster than an organohalosilane that is less attracted to the mobile phase versus the stationary phase. If the difference in elution speeds is large enough, the first and second organohalosilanes can elute partially, mostly, or completely separated from each other as they exit from the chromatographic bed. By collecting the eluate in different fractions, e.g. different portions or parts of the eluate, separation of the first organohalosilane and the second organohalosilane can be achieved. In some embodiments, the fractions can be collected in different containers, for example by changing the container that collects each fraction, or by using switching valves in simulated moving bed techniques. In some embodiments, pressure can be applied against the mobile phase on top of the stationary phase to increase the speed of elution, commonly referred to by one of ordinary skill in the art as flash chromatography, medium-pressure chromatography, or high-pressure chromatography. The pressure can be generated by air pressure pressing against the mobile phase above the stationary phase, or by liquid pressure in the mobile phase above the stationary phase. The liquid pressure can be generated by any suitable means, for example, using a pump.

The eluate can be collected in any suitable number of fractions, as will be readily understood to one of ordinary skill in the art. Any suitable analytical chemistry technique known to one of ordinary skill in the art can be used to detect which fractions contain what proportion of the first and second organohalosilane. At least one of the fractions can be enriched in the first or second organohalosilane. As used herein, a fraction being "enriched" in the first organohalosilane after performing the liquid chromatographic method using a mixture that includes at least a first organohalosilane and a second organohalosilane indicates that the enriched fraction has a greater proportion of the first organohalosilane with respect to the second organohalosilane as compared to the respective proportion in the mixture that was subjected to the method. In an enriched fraction, the amount of the enriched organohalosilane as compared to the other organohalosilane (e.g. the first organohalosilane as compared to the second organohalosilane, or the second organohalosilane as compared to the first organohalosilane), can be more than or equal to about 99.999,999 mol %, 99.999,99 mol %, 99.999,9 mol %, 99.999 mol %, 99.99 mol %, 99.9 mol %, 99 mol %, 98 mol %, 97 mol %, 96 mol %, 95 mol %, 94 mol %, 93 mol %, 92 mol %, 91 mol %, 90 mol %, 85 mol %, 80 mol %, 75 mol %, 70 mol %, 60 mol %, or about 50 mol %.

The method can include recovering the first organohalosilane from the fraction enriched in the first organohalosilane, recovering the second organohalosilane from the fraction enriched in the second organohalosilane, or both. Recovering an organohalosilane from a fraction can include at least partially separating the organohalosilane from the mobile phase that dilutes it. Fractions having a desired organohalosilane enriched to a suitable extent, which can be chosen based on the final desired purity, can be combined. Subsequently, the mobile phase can be removed from the desired organohalosilane using any suitable technique, to provide the purified organohalosilane. Suitable techniques for removal of the mobile phase from an organohalosilane can include, for example, evaporation of the mobile phase from the organohalosilane, or distillation of the organohalosilane from the mobile phase. Any suitable amount of the mobile phase, or any suitable amount of any solvent included in a combination of solvents in the mobile phase, can be removed from the organohalosilane. The mobile phase can be selected to have a differentiable boiling point as compared to the organohalosilane being separated or enriched, to facilitate separation of the organohalosilane and the mobile phase. Recovered organohalosilane can have equal to or less than about 0.000,000,000,000,1 wt % solvent remaining, 0.000,000,001 wt %, 0.000,000,01 wt %, 0.000,000,1 wt %, 0.000,001 wt %, 0.000,01 wt %, 0.000,1 wt %, 0.001 wt %, 0.01 wt %, 0.1 wt %, 1 wt %, 2 wt %, 3 wt %, 4 wt %, 5 wt %, 10 wt %, 20 wt %, 30 wt %, 40 wt % or about 50 wt % solvent remaining.

The organohalosilanes that form the mixture to be separated into enriched fractions can be made in any suitable way. In some embodiments, the mixture to be separated that includes a first organohalosilane and a second organohalosilane is a liquid stream produced by reacting a haloalkane with elemental silicon in the presence of a copper catalyst.

Some embodiments of the present method can provide an organohalosilane having two organic groups, such as dimethyldichlorosilane or dimethylchlorosilane, having less than or equal to about 1000 ppmw of organohalosilanes having one organic group, such as methyltrichlorosilane, or about 900, 800, 700, 600, 500, 400, 300, 200, 100, 75, 50, 25, or less than or equal to about 10 ppmw of an organohalosilane having one organic group. By providing an organohalosilane having two organic groups having low amounts of organohalosilanes having one organic group, some embodiments of the present invention can provide organohalosilanes that can polymerize into linear organopolysiloxanes having a very low amount of branching.

In various embodiments, low amounts of the organohalosilanes to be separated participate in undesired reactions during the separation. In some examples, less than or equal to about 0.000,000,001 wt % of the organohalosilanes to be separated undergo chemical reactions during the separation that change their chemical structure, or 0.000,000,01 wt %, 0.000,000,1 wt %, 0.000,001 wt %, 0.000,01 wt %, 0.000,1 wt %, 0.001 wt %, 0.01 wt %, 0.1 wt %, 1 wt %, 2 wt %, 3 wt %, 4 wt %, 5 wt %, or less than or equal to about 10 wt %.

The liquid-phase chromatography can be any type of liquid-phase chromatography, such as partition chromatography, normal-phase chromatography, displacement chromatography, reversed-phase chromatography, size-exclusion chromatography, ion-exchange chromatography, bioaffinity chromatography, or aqueous normal-phase chromatography. In some embodiments, simulated moved bed chromatography can be used; in other embodiments, simulated moving bed chromatography is not used.

Mobile Phase

The method of the present invention includes passing a liquid mobile phase through the chromatographic bed. The mobile phase can be any suitable mobile phase. The mobile phase can be the same or different as the liquid in the chromatographic bed. In some embodiments, the composition of the mobile phase can be changed during the elution of the mixture, to achieve a desired separation. In some embodiments, the composition of the mobile phase can be changed in a step-wise fashion, with sudden small or large changes in the composition during the elution. For example, in a step-wise variation, the composition of the mobile phase can be changed suddenly from 1:1 hexane:ethyl acetate to 1:4 hexane:ethyl acetate, or can be changed from 100% hexanes to 100% ethyl acetate. In some embodiments, the composition of the mobile phase can be changed as a gradient, with small gradual changes in the composition during the elution. For example, in a gradient, the composition of the mobile phase can be changed from 1:1 hexane:ethyl acetate to 1:2, 1:3, and then 1:4 hexane:ethyl acetate, or even smaller variations can be made between changes. A gradient technique can sometimes result in better separations and can help to avoid cracking of the chromatographic bed caused by heat that can be released when drastically different solvent compositions are allowed to encounter one another and mix in the column as can sometimes occur with a step-wise technique. In other embodiments, a step-wise technique can result in better separations.

The mobile phase can be any suitable organic solvent or combination of organic solvents in any suitable ratio. For example, in various embodiments, the mobile phase can include any one or combination of the following solvents, in any suitable proportion: dimethyl sulfoxide, N,N-dimethylformamide, acetonitrile, acetone, 1,4-dioxane, ethyl acetate, tetrahydrofuran, dichloromethane, diethyl ether, p-xylene, o-xylene, m-xylene, toluene, diisopropyl ether, chloroform, carbon tetrachloride, cyclohexane, pentane, hexanes, heptanes, and any combination thereof. For example, in various embodiments, the mobile phase can include solvent combinations such as, for example, ethyl acetate-hexanes, acetone-hexanes, acetonitrile-methylene chloride, in any suitable proportion.

Normal-Phase Chromatography

In various embodiments of the present invention, the liquid chromatography can be normal-phase chromatography. Normal-phase chromatography can include chromatography in which the stationary phase is relatively polar compared to the mobile phase, such that attraction of a compound being passed through the column to the stationary phase is greater for more polar compounds. Generally in normal-phase chromatography, in the beginning of the elution of the chromatographic bed the mobile phase is chosen to be relatively non-polar and is changed in a step-wise or gradual fashion to be more and more polar until the desired compounds are eluted from the column.

Normal-phase chromatography stationary phases can include any suitable normal-phase chromatography stationary phase. For example, the stationary phase can include silica gel, bonded silica, magnesium silicate, fused silica, Florosil™, alumina, polymer media (e.g. hydrophilic or polar polymer), resin, dialkyl phthalate, tetrachlorophthalate, polyethylene glycol, or any combination thereof. Other examples can include bonded silica, wherein the silica is functionalized with a relatively polar functional group to modify its polarity, such as aminoalkyl-bonded silica, diol-bonded silica (e.g. dihydroxyalkyl-bonded, dihydroxyalkoxyalkyl-bonded), or cyanoalkyl-bonded silica. In some examples, the silica can be bonded to a suitable functional group, for example directly (e.g. Si—O—R') or as an —O—SiR$_2$—R' group, wherein R independently designates any alkyl group, such as a C$_{1-6}$ alkyl group, such as methyl or ethyl, and wherein R' denotes a suitable functional group such as alkyl, hydroxyalkyl, cyanoalkyl, or the like. In some examples, bonded silica can be prepared by treating silica with a compound that reacts with the —OH groups on silica, such as a compound having the structure X—SiR$_2$—R', wherein X denotes a halide or other suitable leaving group. In some examples, the polarity of the stationary phase can be modified by treating the stationary phase with a column modifier, such as for example, water, acetic acid, aqueous ammonium hydroxide, formic acid, phosphoric acid, aqueous sodium hydroxide, silver nitrate, triethylamine, trifluoroacetic acid. The column modifier can be washed out of the column using the mobile phase prior to eluting the mixture to be separated through the column.

Reverse-Phase Chromatography

In various embodiments of the present invention, the liquid chromatography can be reverse-phase chromatography. Reverse-phase chromatography can include chromatography in which the stationary phase is relatively non-polar compared to the mobile phase, such that the attraction of a compound being passed through the column to the stationary phase is less for more polar compounds. Generally in reverse-phase chromatography, in the beginning of the elution of the chromatographic bed the mobile phase is chosen to be relatively polar and is changed in a step-wise or gradual fashion to be more and more non-polar until the desired compounds are eluted from the column.

Reversed-phase chromatography stationary phases can include any suitable reversed-phase chromatography stationary phase. For example, the stationary phase can include bonded silica, resin, polymer media, polystyrene, polystyrene-polydivinylbenzene copolymer, or any combination thereof. The bonded silica can be silica bonded to a suitable non-polar functional group. In some examples, the silica can be bonded to a suitable functional group, for example directly (e.g. Si—O—R') or as an —O—SiR$_2$—R' group, wherein R independently designates any alkyl group, such as a C$_{1-6}$ alkyl group, such as methyl or ethyl, and wherein R' denotes a suitable functional group such as any C$_{1-50}$ alkyl group. For example, the bonded silica can be C8 or C18 bonded silica, which can include silica bound to —O—SiR$_2$—(CH$_2$)$_7$CH$_3$ or —O—SiR$_2$—(CH$_2$)$_{17}$CH$_3$ groups, respectively, wherein R in this paragraph can independently designate any alkyl group, such as a C$_{1-6}$ alkyl group, such as methyl or ethyl.

Simulated Moving Bed or Sequential Simulated Moving Bed

In various embodiments, the method can include the use of a moving bed or a simulated moving bed. A simulated moving bed is a chromatography technique that can be used to lengthen a finite length stationary phase to essentially any desired length in order to achieve any suitable desired degree of separation. The technique can allow more efficient use of stationary phase and mobile phase to achieve a given separation. The technique can include employing a plurality of columns connected in series and a valve arrangement including multiple inlets and outlets. A sequential simulated moving bed technique is the use of a sequential combination of several sequential simulated moving bed techniques that can allow for increases in efficiency of separation and purity of the resulting products.

For example, a simulated moving bed setup can include multiple columns arranged in a circular loop configuration (e.g. at least two or more columns), with the junction between each two columns having a valve through which solvent or sample can be injected or withdrawn, or through which material can be allowed to flow from one column to the next. The solvent can be pumped continuously through the loop, to form a closed system. The mixture injection point, the mobile phase injection point, and one or more withdrawal points can be suitably selected from the valves in the system that occur between the columns. Suitable examples of simulated moving bed chromatography and sequential simulated moving bed chromatography methods are described in, for example, Pedro Sá Gomes; Alírio E. Rodrigues; Chem. Eng. Technol. 2012, 35, No. 1, 17-34.

The present invention can be better understood by reference to the following examples which are offered by way of illustration. The present invention is not limited to the examples given herein.

EXAMPLE 1

Reversed-Phase

Silicone tubing was connected to the end of a 10 ml graduated glass pipette and the end was closed off using a hose clamp. A small plug of quartz wool was placed at the bottom of the column in order to retain the stationary phase (Silica gel C18 Reverse Phase—Fluka Analytical, particle size=about 15-25 µm, pore size=about 10 nm, surface area=about 380 $m^2$/g). The materials were then transferred to a glove box for subsequent steps. Three milliliters of the mobile phase (99.8% acetonitrile—anhydrous from Sigma Aldrich) was added to the column. Next, a slurry of the stationary phase in acetonitrile was added. The stationary phase was allowed to slowly settle out to the bottom of the column. The hose clamp was periodically opened to allow liquid to drain out of the column so that additional slurry could be added. The process was stopped once a 5.5 inch long stationary phase bed had been established.

Prior to starting the experiment, the liquid level was drained to be even with the top of the bed and approximately 0.4 ml of a 50:50 volume feed mixture of methyltrichlorosilane (99%, Aldrich) and dimethyldichlorosilane (99+%, Fluka) was added to the column. Additional liquid was removed until the liquid level was even with the top of the bed. Six milliliters of mobile phase was then added to the top of the column and the hose clamp was removed to allow flow out of the bottom of the column. A 6 ml syringe connected to a three-way valve was then connected to the top of the column via silicone tubing and the syringe was compressed in order to pressurize the column to increase the flow rate. Next, 3 ml of solution was drained off of the column to waste. The remaining volume coming off of the column was collected in 10 droplet (~0.25 ml) fractions. The fractions were sealed in vials with septa and transferred out of the glove box in order to carry out analysis.

Samples were analyzed using a manual headspace injection method on a gas chromatography system (Agilent 7890A with Agilent LTM system). A constant temperature (70° C.), constant pressure (60.688 kPa) program was run using a SPB-octyl capillary column—30 m×0.25 mm×0.25 µm (Supelco). Peak areas were manually integrated using the signal from the TCD detector. Three replicate injections were run on each sample fraction.

FIG. 1 illustrates that separation of dimethyldichlorosilane and methyltrichlorosilane occurs in the liquid chromatography column. FIG. 1 illustrates the ratio of dimethyldichlorosilane to methyltrichlorosilane in the eluate from the liquid chromatography column as measured by peak area ratios from GC-TCD of the collected elution fractions. The ratio of dimethyldichlorosilane to methyltrichlorosilane in the original feed injected onto the liquid chromatography column is provided for reference (dashed line, concentrations of both components in the feedstock also determined by GC-TCD).

EXAMPLE 2

Normal-Phase

A column prepared similarly to that in Example 1, wherein the stationary phase was Florisil (100-200 mesh from Sigma Aldrich, surface area=about 289 $m^2$/g) and the mobile phase was heptane (Reagent Grade from Fisher Scientific). The feed to the column consisted of a 50:50 volume mixture of dimethylchlorosilane (98%, Aldrich) and methyltrichlorosilane (99%, Aldrich). FIG. 2 demonstrates that separation of the dimethylchlorosilane and methyltrichlorosilane were achieved by comparing several elution fractions from the column as measured by GC-TCD with the ratio of TCD peaks present in the reference feedstock.

FIGS. 2A, 2B, 2C, and 2D illustrate the feedstock and elution fractions 5, 9 and 12 from the liquid chromatography column, respectively, showing different ratios of dimethylchlorosilane to methyltrichlorosilane as measured by GC-TCD peak area ratios when compared to the feedstock mixture of dimethylchlorosilane and trichloromethylsilane that was injected onto the liquid chromatography column.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

ADDITIONAL EMBODIMENTS

The present invention provides for the following exemplary embodiments, the numbering of which is not to be construed as designating levels of importance:

Embodiment 1 provides a liquid chromatography method for separating organohalosilanes, the method including: introducing a mixture including at least a first organohalosilane and a second organohalosilane onto a chromatographic bed including a stationary phase; and passing a liquid mobile phase through the chromatographic bed to produce an eluate including at least one fraction enriched in the first organohalosilane and at least one fraction enriched in the second organohalosilane.

Embodiment 2 provides the method according to Embodiment 1, wherein the chromatographic bed forms a column.

Embodiment 3 provides the method according to any of the preceding Embodiments, further including recovering the first organohalosilane from the fraction enriched in the first organohalosilane, recovering the second organohalosilane from the fraction enriched in the second organohalosilane, or any combination thereof.

Embodiment 4 provides the method according to any of the preceding Embodiments, wherein the mobile phase includes dimethyl sulfoxide, N,N-dimethylformamide, acetonitrile, acetone, 1,4-dioxane, ethyl acetate, tetrahydrofuran, dichloromethane, diethyl ether, p-xylene, o-xylene, m-xylene, toluene, diisopropyl ether, chloroform, carbon tetrachloride, cyclohexane, pentane, hexanes, heptanes, or any combination thereof.

Embodiment 5 provides the method according to any of the preceding Embodiments, wherein the chromatography method is a normal-phase chromatography method.

Embodiment 6 provides the method according to Embodiment 5, wherein the stationary phase includes silica gel, bonded silica, fused silica, Florosil™, alumina, polymer media, resin, dialkyl phthalate, tetrachlorophthalate, polyethylene glycol, or any combination thereof.

Embodiment 7 provides the method according to any of the preceding Embodiments, wherein the chromatography method is a reversed-phase chromatography method.

Embodiment 8 provides the method according to Embodiment 7, wherein the stationary phase includes bonded silica, resin, polymer media, polystyrene, polystyrene-polydivinylbenzene copolymer, or any combination thereof.

Embodiment 9 provides the method according to Embodiment 7, wherein the stationary phase includes a bonded silica.

Embodiment 10 provides the method according to Embodiment 9, wherein the bonded silica includes at least one alkyl-bonded silica.

Embodiment 11 provides the method according to Embodiment 10, wherein the alkyl-bonded silica includes C8 bonded silica or C18 bonded silica.

Embodiment 12 provides the method according to any of the preceding Embodiments, wherein the chromatography method includes a simulated moving bed chromatography method or sequential simulated moving bed chromatography method, wherein the method employs a plurality of columns connected in series and a valve arrangement including multiple inlets and outlets.

Embodiment 13 provides the method according to any of the preceding Embodiments, wherein the composition of the liquid mobile phase is varied continuously or step-wise during the elution.

Embodiment 14 provides the method according to any of the preceding Embodiments, wherein the mixture is a liquid stream produced by reacting a haloalkane with elemental silicon in the presence of a copper catalyst.

Embodiment 15 provides the method according to any of the preceding Embodiments, wherein the first organohalosilane is selected from dimethydichlorosilane and dimethylchlorosilane, and the second organohalosilane is methyltrichlorosilane.

Embodiment 16 provides the method according to any of the preceding Embodiments, wherein the mobile phase is passed through the chromatographic bed under an applied pressure.

Embodiment 17 provides the method according to any of the preceding Embodiments, wherein the mixture includes dimethyldichlorosilane and methyltrichlorosilane in a mole ratio of from about $10^6$:1 to about $10^{-6}$:1.

Embodiment 18 provides the method according to any of the preceding Embodiments, wherein the mixture includes dimethylchlorosilane and methyltrichlorosilane in a mole ratio of from about $10^6$:1 to about $10^{-6}$:1.

Embodiment 19 provides the first or second organohalosilane separated by the method of Embodiment 1.

Embodiment 20 provides a liquid chromatography method for separating organohalosilanes, the method including: introducing a mixture including at least dimethydichlorosilane and methyltrichlorosilane onto a chromatographic bed including a stationary phase, the mixture including dimethyldichlorosilane and methyltrichlorosilane in a mole ratio of from about $10^6$:1 to about $10^{-6}$:1; passing a liquid mobile phase through the chromatographic bed to produce an eluate including at least one fraction enriched in dimethydichlorosilane and a fraction enriched in methyltrichlorosilane; and recovering the at least one fraction enriched in dimethydichlorosilane and the at least one fraction enriched in methyltrichlorosilane.

Embodiment 21 provides the apparatus or method of any one or any combination of Embodiments 1-20 optionally configured such that all elements or options recited are available to use or select from.

We claim:

1. A liquid chromatography method for separating organohalosilanes, the method comprising:
   introducing a mixture comprising at least a first organohalosilane and a second organohalosilane onto a chromatographic bed comprising a stationary phase, wherein the stationary phase comprises silica gel, bonded silica, fused silica, magnesium silicate, alumina, dialkyl phthalate, tetrachlorophthalate, polyethylene glycol, or any combination of two or more of silica gel, bonded silica, fused silica, magnesium silicate, alumina, dialkyl phthalate, tetrachlorophthalate, and polyethylene glycol; and
   passing a liquid mobile phase through the chromatographic bed to produce an eluate comprising at least one fraction enriched in the first organohalosilane and at least one fraction enriched in the second organohalosilanes.

2. The method according to claim 1, wherein the chromatographic bed forms a column.

3. The method according to claim 1, further comprising recovering the first organohalosilane from the fraction enriched in the first organohalosilane, recovering the second organohalosilane from the fraction enriched in the second organohalosilane, or any combination thereof.

4. The method according to claim 1, wherein the mobile phase comprises dimethyl sulfoxide, N,N-dimethylformamide, acetonitrile, acetone, 1,4-dioxane, ethyl acetate, tetrahydrofuran, dichloromethane, diethyl ether, p-xylene, o-xylene, m-xylene, toluene, diisopropyl ether, chloroform, carbon tetrachloride, cyclohexane, pentane, hexanes, heptanes, or any combination of two or more of dimethyl sulfoxide, N,N-dimethylformamide, acetonitrile, acetone, 1,4-dioxane, ethyl acetate, tetrahydrofuran, dichloromethane, diethyl ether, p-xylene, o-xylene, m-xylene, toluene, diisopropyl ether, chloroform, carbon tetrachloride, cyclohexane, pentane, hexanes, or heptanes.

5. The method according to claim 1, wherein the chromatography method is a normal-phase chromatography method.

6. The method according to claim 1, wherein the chromatography method is a reversed-phase chromatography method.

7. The method according to claim 6, wherein the stationary phase comprises a bonded silica.

8. The method according to claim 7, wherein the bonded silica comprises at least one alkyl-bonded silica.

9. The method according to claim 8, wherein the alkyl-bonded silica comprises C8 bonded silica or C18 bonded silica.

10. The method according claim 1, wherein the chromatography method comprises a simulated moving bed chromatography method or sequential simulated moving bed chromatography method, wherein the method employs a plurality of columns connected in series and a valve arrangement comprising multiple inlets and outlets.

11. The method according claim 1, wherein the composition of the liquid mobile phase is varied continuously or step-wise during the elution.

12. The method according to claim 1, wherein the first organohalosilane is selected from dimethydichlorosilane and dimethylchlorosilane, and the second organohalosilane is methyltrichlorosilane.

13. A liquid chromatography method for separating organohalosilanes, the method comprising:

introducing a mixture comprising at least dimethydichlorosilane and methyltrichlorosilane onto a chromatographic bed comprising a stationary phase, the mixture comprising dimethyldichlorosilane and methyltrichlorosilane in a mole ratio of from about $10^6$:1 to about $10^{-6}$:1, and the stationary phase comprising silica gel, bonded silica, fused silica, magnesium silicate, alumina, dialkyl phthalate, tetrachlorophthalate, polyethylene glycol, or any combination of two or more of silica gel, bonded silica, fused silica, magnesium silicate, alumina, dialkyl phthalate, tetrachlorophthalate, and polyethylene glycol;

passing a liquid mobile phase through the chromatographic bed to produce an eluate comprising at least one fraction enriched in dimethydichlorosilane and a fraction enriched in methyltrichlorosilane; and recovering the at least one fraction enriched in dimethydichlorosilane and the at least one fraction enriched in methyltrichlorosilane.

\* \* \* \* \*